United States Patent [19]

Kam et al.

[11] Patent Number: 4,604,481

[45] Date of Patent: Aug. 5, 1986

[54] COMPOUNDS FOR TREATMENT OR PROPHYLAXIS OF CARDIAC DISORDERS

[75] Inventors: Sheung-tsam Kam, Vernon Hills; Paul W. Erhardt; Robert J. Borgman, both of Mundelein, all of Ill.; John P. O'Donnell, Morgantown, W. Va.

[73] Assignee: American Hospital Supply Corporation, Evanston, Ill.

[21] Appl. No.: 490,476

[22] Filed: May 25, 1983

Related U.S. Application Data

[62] Division of Ser. No. 211,341, Nov. 28, 1980, Pat. No. 4,405,642.

[51] Int. Cl.$^4$ .................. C07C 101/42; C07C 101/30
[52] U.S. Cl. ...................................... 560/39; 560/106; 560/110
[58] Field of Search .......................... 560/110, 39, 106

[56] References Cited

U.S. PATENT DOCUMENTS 3,501,769  3/1970  Crowther et al. ............. 260/501.17
4,402,974  9/1983  Matier et al. ........................ 424/308
4,405,642  9/1983  Kam et al. ............................ 424/309

FOREIGN PATENT DOCUMENTS 48-2264   3/1973  Japan .
48-22465  3/1973  Japan .

OTHER PUBLICATIONS

Tatsuno et al., *J. Med. Chem.*, vol. 20, 394-397 (1977).
O'Donnell et al., *J. Pharm. Sci.*, 68, 1236-1238 (1979).

Primary Examiner—Bernard Helfin
Attorney, Agent, or Firm—Bernard, Rothwell & Brown

[57] ABSTRACT

A method for the treatment or prophylaxis of cardiac disorders in a mammal, comprising administering to such mammal a short-acting β-blocking compound of the formula:

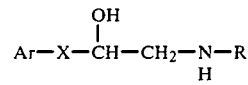

wherein X is an ester-containing group; R may be lower alkyl, aralkyl or an ester-containing group; $R_1$ may be lower alkyl; and Ar may be substituted or unsubstituted aromatic; or a pharmaceutically acceptable salt thereof. Novel compounds possessing short acting β-adrenergic blocking activity are also disclosed.

16 Claims, No Drawings

COMPOUNDS FOR TREATMENT OR PROPHYLAXIS OF CARDIAC DISORDERS

This is a division of application Ser. No. 211,341, filed Nov. 28, 1980 and now U.S. Pat. No. 4,405,642.

BACKGROUND OF THE INVENTION

The present invention relates to compounds for the treatment or prophylaxis of cardiac disorders. More particularly, the invention relates to a novel β-adrenergic blocking compounds for the treatment of prophylaxis of cardiac disorders.

The therapeutic and prophylactic uses of compounds which block sympathetic nervous stimulation of β-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus reducing heart work can aid in the prevention of further tissue damage and can relieve angina pectoris.

β-Adrenergic stimulation may also aggravate or cause arrhythmias because of increased levels of catecholamines. Thus β-blocking agents may be employed to reduce the risks of arrhythmias.

Compounds have been discovered which selectively block β-adrenergic receptors in various organs. Beta receptors in the heart are generally referred to as $\beta_1$ receptors, and those associated with vasodilation and bronchodilation are $\beta_2$ receptors. Selective $\beta_1$-blockers are preferred for the treatment of cardiac disorders because they may have less potential to cause hypertension or bronchoconstriction. A number of $\beta_1$ selective adrenergic blocking agents have been discovered. Smith, L. H., *J. Appl. Chem. Biotechnol.*, 28, 201–212 (1978). Most of such compounds are structural variations of 1-amino-3-aryloxy-2-propanol.

Heretofore, the emphasis in β-blocker research has been to develop compounds which can be administered to cardiac patients over long periods of time. However, often it is desirable in the critical care setting to quickly reduce heart work or improve rhythmicity during a cardiac crisis, e.g., during or shortly after a myocardial infarction. Conventional β-blocking agents can be employed for such treatment, but their duration of action may be much longer than desired by the physician. A β-blocking agent possessing a long duration of action does not allow precise control of heart work or prompt reversal of the β-blocking effect, which may be required in a critical care setting. For instance, if heart output becomes dangerously low, it is desirable to quickly reduce or eliminate β-blocking activity. The lingering activity of available β-blocking agents can be counterproductive and can greatly complicate the therapeutic decisions required of the physician during such critical care of cardiac patients.

Accordingly, there is a need for a pharmaceutical preparation and method of treatment, employing a β-adrenergic blocking agent having a short duration of action.

SUMMARY OF THE INVENTION

In accordance with the present invention, disclosed herein are short-acting, β-adrenergic blocking compounds of the formula

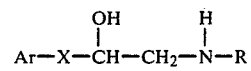

wherein Ar is unsubstituted phenyl or phenyl substituted with fluoro in the ortho position or phenyl substituted with methyl in the meta or para position; X is

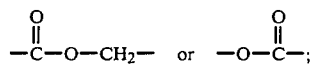

and R is isopropyl, t-butyl or 3,4-dimethoxyphenethyl; with the proviso that when Ar is unsubstituted phenyl, R is isopropyl or 3,4-dimethoxyphenethyl; and with the further proviso that when X is

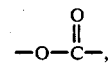

Ar is unsubstituted phenyl and R is 3,4-dimethoxyphenyl; or a pharmaceutically acceptable salt thereof.

DETAILED DESCRIPTION OF THE INVENTION

Compounds administered by the method of the present invention are represented by the formula:

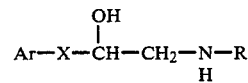

wherein X represents an ester function of the formula

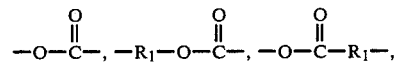

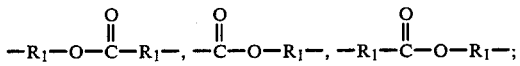

R represents lower alkyl of straight and branched carbon chains from 1 to about 10 carbon atoms; cycloalkyl of from 3 to 7 carbon atoms; alkenyl of from 3 to 10 carbon atoms, aralkyl or aryloxyalkyl wherein the alkyl portion contains from about 1 to about 5 carbon atoms and the aryl portion represents substituted or unsubstituted monocyclic or polycyclic aromatic or heterocyclic ring systems of from 6 to about 10 carbon atoms, such as 3,4-dimethoxyphenethyl, 4-carbamoylphenoxyethyl, 1,1-dimethyl-2-(3-indolyl) ethyl and the like; $R_1$ represents lower alkyl of from 1 to about 5 carbon atoms, and Ar represents substituted or unsubstituted aromatic, including monocyclic, polycyclic and heterocyclic ring systems. When two or more groups of the same designation occur in the same formula, it is not necessary that those groups be identical. Aromatic (Ar) substituents may include lower alkyl, lower alkenyl, lower alkynyl, lower alkoxy, halogen, acetamido, amino, nitro, lower alkylamino, hydroxyl, hydroxyalkyl, cyano, and groups of the formula

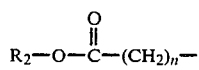

wherein $R_2$ is lower alkyl, aryl or aralkyl and n is an integer from 0 to about 10. The compounds described herein are not limited to any particular stereoisomeric configuration. Such compounds may be administered as their pharmaceutically acceptable addition salts, e.g., as the hydrochloride, sulfate, phosphate, oxalate, gluconate, tartrate, etc.

In preferred compounds, R is lower alkyl of from 1 to about 5 carbon atoms, such as isopropyl, t-butyl; or aralkyl wherein the alkyl portion contains from 1 to about 3 carbon atoms and the aryl portion contains from 6 to about 10 carbon atoms, such as 3,4-dimethoxyphenethyl; $R_1$ is methylene; and Ar is unsubstituted phenyl, or phenyl substituted with lower alkyl of from 1 to about 5 carbon atoms, fluoro, chloro, nitro, or a group of the formula

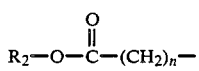

wherein $R_2$ is lower alkyl of from 1 to about 5 carbon atoms and n is an integer from 0 to about 5. In particularly preferred embodiments of the present invention, X is

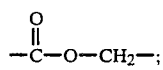

R is selected from the group consisting of isopropyl, t-butyl, and 3,4-dimethoxyphenethyl, and Ar is unsubstituted phenyl or phenyl substituted with methyl, fluoro, chloro, or nitro.

In an alternative embodiment, the amine substituent, R, may also include ester-containing groups. For instance, R may be of the formula

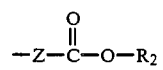

wherein Z is a straight or branched chain hydrocarbon of from 1 to about 10 carbon atoms.

The compounds described herein may be prepared by a number of synthetic methods, depending upon the particular structure desired. Four reaction schemes are described for various configurations of the ester function, X.

For compounds of the formulas hereinbefore described in which X is

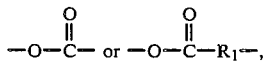

the following reaction scheme may be employed:

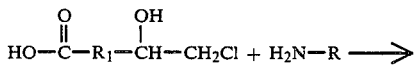

-continued

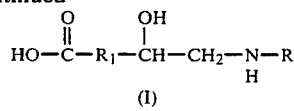

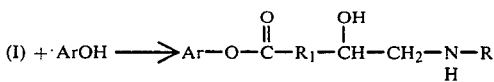

In the above scheme, $R_1$ is eliminated when X is

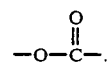

Suitable protective groups are advantageously reacted with the hydroxyl or amino groups as is well known in the art. For example, the amino group of compound I may be reacted with p-methoxybenzyloxycarbonyl azide to form the N-p-methoxybenzyloxycarbonyl derivative, and the hydroxy acid may be reacted with dihydropyran followed by selective cleavage of the tetrahydropyranyl ester to yield the free acid. The protective groups may be cleaved from the aryl compound, e.g., by treatment with a mineral acid.

For compounds in which X is

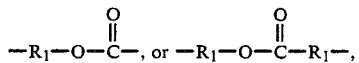

the following reaction scheme may be employed:

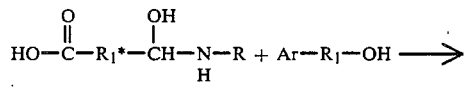

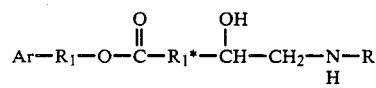

*eliminated when X is $-R_1-O-\overset{O}{\underset{\|}{C}}-$

Compounds in which Ar is not substituted with an ester-containing group and in which X is

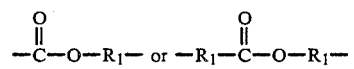

are advantageously prepared by either of the following two schemes:

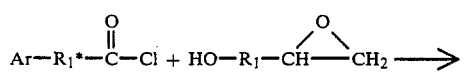

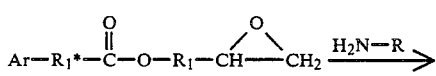

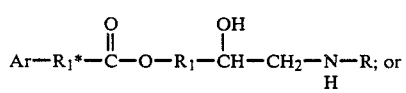

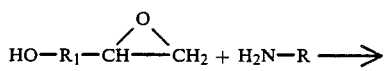

-continued

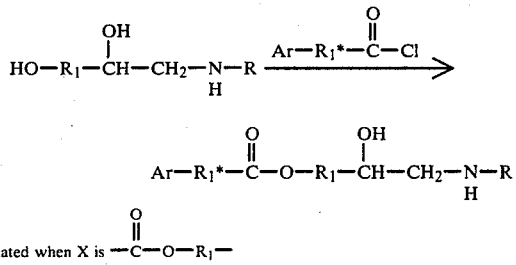

*eliminated when X is —C—O—R₁—

This latter scheme is particularly preferred for compounds in which R is an ester-containing group.

The compounds of this invention are advantageously administered parenterally, e.g., by intravenous injection or intravenous infusion. Formulations for intravenous injection preferably include the active compound as a soluble acid addition salt in a properly buffered isotonic solution.

The dosage administered to a patient and the duration of infusion will depend upon the patient's needs and the particular compounds employed. For short periods of infusion, e.g. less than about three hours, the duration of effect is thought to be determined by both metabolic effects and distribution phenomena. For relatively long periods of infusion, e.g. greater than about three hours, the duration of effect is thought to depend largely on metabolic effects. Accordingly, although the present methods and compounds are generally useful for short term infusion therapy, certain compounds are preferred for longer durations of infusion. This principle is demonstrated by reference to the 40 minute and three hour infusion studies described in Examples LXXX–CIV. The compounds have been found to be generally nontoxic within conventional dosage ranges. Dosages of from about 0.001 to about 100 mg. per kg. of body weight per hour are generally employed, with preferred dosages ranging from about 0.01 to about 10 mg. per kg. of body weight per hour.

The compounds of the present invention have a relatively short duration of action compared to conventional β-blockers. In vitro studies in human whole blood indicate that the ester functions are subject to rapid enzymatic cleavage, resulting in inactive metabolites. Compounds of the present invention in which the amine substituent, R, contains an ester function, have two potentially labile sites for enzymatic hydrolysis. Thus the β-blocking activity can be carefully controlled by regulating dosage size and rate of administration. The time required for substantially complete disappearance of the β-blocking effects of the compounds of the present invention ranges from about 5–10 minutes to about 1 hour or more. Generally, it is preferred that the recovery is accomplished within about ten to fifteen minutes. A short acting β-blocker can advantageously be infused at a rate sufficient to provide the desired action, e.g., titrated to the specific patient's needs, and such action can be promptly discontinued by stopping the infusion. Thus, the method of the present invention provides a very useful therapeutic alternative in the treatment or prophylaxis of cardiac disorders.

The present invention is further illustrated by the following examples which are not intended to be limiting.

EXAMPLE I

This example describes the synthesis of a compound of the following formula:

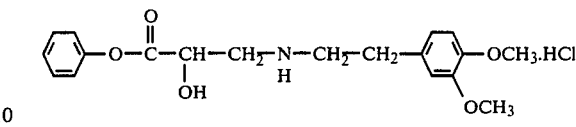

3-[(3,4-Dimethoxyphenethyl)amino]-2-hydroxypropionic Acid

A mixture of 20 g (0.16 mole) of β-chlorolactic acid and 86 g (0.48 mole) of 3,4-dimethoxyphenethylamine was heated at 110° C. for 15 hours. The resulting product was dissolved in about 200 ml of water and the pH was adjusted to about 8 with $Na_2CO_3$. The aqueous solution was extracted with 2×500 ml of chloroform and neutralized to pH 7 with diluted HCl. The solution was evaporated to dryness and the residue was recrystallized in EtOH to give 24.6 g (61.6%) of crystals: m.p. 187.5°–188.5° C. The NMR, IR and mass spectra were consistent with the assigned structure, and the elemental analysis was consistent with the empirical formula, $C_{13}H_{19}O_5N$.

3-[[N-(3,4-Dimethoxyphenethyl)-N-(4-methoxybenzyloxycarbonyl)]amino]-2-hydroxypropionic Acid To a solution of 0.245 g (0.91 mmole) of the amino acid from the previous experiment in 10 ml of dioxane-$H_2O$ (1:1) was added 0.23 g (2.73 mmole) of $NaHCO_3$ and 0.19 g (0.92 mmole) of p-methoxybenzyloxycarbonyl azide. The reaction mixture was stirred at room temperature for 16 hours and extracted between 20 ml of water and 2×20 ml of ether. Evaporation of the ether gave 0.08 g (36%) of the product. The NMR and IR spectra were consistent with the assigned structure.

3-[[N-(3,4-Dimethoxyphenethyl)-N-(4-methoxybenzyloxycarbonyl)]amino]-2-[(tetrahydro-2-pyranyl)oxy]-propionic Acid To 3.6 g (8.9 mmole) of the α-hydroxy acid from the previous experiment in 20 ml of methylene chloride was added 3.74 g (44.5 mmole) of dihydropyran and a catalytic amount of p-toluenesulfonic acid. The reaction mixture was stirred at room temperature for 3 hours and neutralized with concentrated $NH_4OH$. The reaction mixture was filtered and the solvent was evaporated. The residue was stirred with 70 ml ether and 0.3 ml of HCl at room temperature for 1 hour, neutralized with $NH_4OH$, filtered, and the ether was removed in vacuo to afford 3.92 g (90.1%) of product. The NMR and IR spectra were consistent with the assigned structure.

Phenyl 3-[[N-(3,4-Dimethoxyphenethyl)-N-(4-methoxybenzyloxycarbonyl)]amino]-2-[(tetrahydro-2-pyranyl)oxy]-propionate A solution, which consisted of 3.92 g (7.5 mmole) of the acid from the previous experiment, 30 ml of THF and 1.48 g (9 mmole) of carbonyldiimidazole was stirred at room temperature for 0.5 hour. To the reaction mixture was added 0.855 g (10.5 mmole) of phenol and a catalytic amount of sodium imidazole. The reaction mixture was stirred for 10 hours and partitioned between 2×100 ml of ether and 100 ml of water. Evaporation of the ether gave an oil which was purified by column chromatography (silica gel/EtOAc: hexane=1:1) to give 1.1 g (24%) of oil product. The NMR and IR spectra were consistent with the assigned structure and the elemental analysis was consistent with the empirical formula $C_{33}H_{39}O_9N$.

N-(3,4-Dimethoxyphenethyl)-N-[(2-hydroxy-2-phenoxycarbonyl)ethyl-]amine Hydrochloride A mixture of 1 g of the propionate from the previous experiment and 50 ml of 2% HCl in ether was stirred at room temperature for 2 hours. The precipitate was collected by filtration and recrystallized in 2-propanol to give 0.3 g (46.6%) of white crystals: m.p. 150.5°–151° C. The NMR, IR and MS spectra were consistent with the assigned structure and the elemental analysis was consistent with the empirical formula $C_{19}H_{24}O_5NCl$.

EXAMPLES II–IV

The compounds described in the following table were produced by substantially the same procedure as that described in Example I, except that the aryl hydroxy reactants shown in Table I were substituted for phenol. The reaction products were purified by recrystallization from 2-propanol, to yield the indicated products which were identified by NMR and IR spectroscopy, elemental analysis, and melting point.

TABLE I

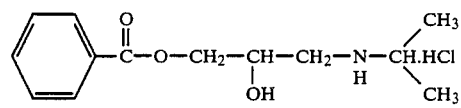

| Example | Ar—OH | Ar | Melting Point |
|---|---|---|---|
| II | 3-methylphenol | 3-methylphenyl | 116–117° C. |
| III | 2,6-dimethylphenol | 2,6-dimethylphenyl | 171–171.5° C. |
| IV | 1-naphthol | 1-naphthyl | 151° C. |

EXAMPLE V

This example describes the synthesis of a compound of the following formula:

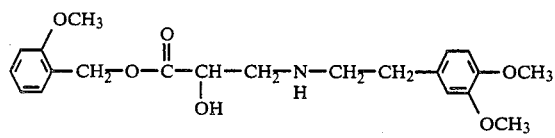

2-Methoxybenzyl 3-[[N-(3,4-Dimethoxyphenethyl)]amino]-2-hydroxypropionate

To 3 g of the 3-(3,4-dimethoxyphenethyl)amino-2-hydroxypropionic acid prepared in Example I was added 200 ml of benzene and 20 ml of 2-methoxybenzyl alcohol. About 0.5 ml of concentrated HCl was added to catalyze the reaction. The reaction mixture was heated to reflux for 6 hours and the water was collected by a moisture trap. The reaction mixture was extracted with 200 ml of 0.5% HCl in water. The aqueous layer was basified with $NaHCO_3$ and extracted with $CHCl_3$. Evaporation of the $CHCl_3$ gave an oily residue which after chromatography on a column (silica gel/Et$_2$O:EtOH=5:1) gave 1 g (23%) of white solid: m.p. 79.5°–82.5° C. The NMR, IR and mass spectra were consistent with the assigned structure and the elemental analysis was consistent with the empirical formula $C_{21}H_{27}O_6N$.

EXAMPLE VI

This example describes the synthesis of a compound of the formula:

$$\text{Ph-C(=O)-O-CH}_2\text{-CH(OH)-CH}_2\text{-N(H)-CH(CH}_3\text{)}_2 \cdot \text{HCl}$$

2,3 Epoxypropyl Benzoate

A mixture containing 14.8 g (0.2 mole) of glycidol, 150 ml of anhydrous ether, 16 g (0.4 mole) of pyridine and 28 g (0.2 mole) of benzoyl chloride was stirred at room temperature for 2 hours. The mixture was filtered and the ether was evaporated to leave an oil. This oil was distilled to give 21 g (60%) of colorless oil: b.p. 92° C./0.5 mm Hg. The NMR and IR spectra were consistent with the assigned structure.

[3-(Isopropylamino)-2-hydroxy]propyl Benzoate Hydrochloride

To 1 g of the epoxide from the previous experiment was added 10 g of isopropylamine. The resultant solution was refluxed for 16 hours and evaporated to dryness. The oily residue was chromatographed on a column (silica gel/EtOH:CH$_2$Cl$_2$=1.5:3.5) to afford 0.35 g (22%) of the product (free amine). The amine was converted to its HCl salt by addition of etheral HCl. The amine salt was collected by filtration and recrystallized in 2-propanol to give white crystals: m.p. 155.5°–156.5° C. The NMR and IR spectra were consistent with the assigned structure and the elemental analysis was consistent with the empirical formula $C_{13}H_{26}O_3NCl$.

EXAMPLES VII–XIII

The experiment of Example VI was repeated in all essential details to produce the compounds described in Table II, except that the reactants described in the second and third columns of the table were substituted for benzoyl chloride and isopropyl amine respectively. The compound of Example VIII was purified by recrystallization from acetone, and the compound of Example IX was purified by recrystallization from toluene. All of the compounds were prepared as the hydrochloride salts except the compound of Example IX which was the free base. Each of the compounds was identified by NMR and IR spectroscopy, elemental analysis, and melting point.

TABLE II $$Ar-\overset{O}{\underset{\|}{C}}-O-CH_2-\overset{OH}{\underset{|}{CH}}-CH_2-\underset{H}{\overset{|}{N}}-R$$

| Example | Ar−$\overset{O}{\underset{\|}{C}}$−Cl | R−NH$_2$ | Ar | R | Melting Point |
|---|---|---|---|---|---|
| VII | benzoyl chloride | 3,4-dimethoxyphenethyl amine | phenyl | 3,4-dimethoxyphenethyl | 130° C. |
| VIII | 3-methylbenzoyl chloride | isopropylamine | 3-methylphenyl | isopropyl | 137.5–138° C. |
| IX | 3-methylbenzoyl chloride | 3,4-dimethoxyphenethyl amine | 3-methylphenyl | 3,4-dimethoxyphenethyl | 88.5° C. |
| X | 4-methylbenzoyl chloride | isopropylamine | 4-methylphenyl | isopropyl | 151.5–152° C. |
| XI | 4-methylbenzoyl chloride | 3,4-dimethoxyphenethyl amine | 4-methylphenyl | 3,4-dimethoxyphenethyl | 153–153.5° C. |
| XII | 2-chlorobenzoyl chloride | isopropylamine | 2-chlorophenyl | isopropyl | 129° C. |
| XIII | 2-chlorobenzoyl chloride | 3,4-dimethoxyphenethyl amine | 2-chlorophenyl | 3,4-dimethoxyphenethyl | 113.5–114° C. |

EXAMPLE XIV

This example describes an alternate synthesis of the compound in Example XII.

3-(Isopropylamino)-1,2-propanediol

A mixture of 37 g (0.5 mole) of glycidol and 35.4 g (0.6 mole) of isopropylamine was stirred at 25° overnight. Excess isopropylamine was evaporated in vacuo and the mixture was distilled to give 53 g of product: b.p. 80° C./0.1 mm Hg. The NMR and IR spectra were consistent with the assigned structure and the elemental analysis was consistent with the empirical formula C$_6$H$_{15}$O$_2$N.

[3-(Isopropylamino)-2-hydroxy]propyl 2-chlorobenzoate hydrochloride

A solution of 10 g (75 mmole) of the diol from the previous experiment and 5.9 g (75 mmole) of pyridine hydrochloride in 20 ml of pyridine was treated with 13.1 g (75 mmole) of 2-chlorobenzoyl chloride. The mixture was stirred at room temperature for 2 hours and 100 ml of water was added. The pyridine was evaporated in vacuo at 55°–60° C. and the aqueous solution was washed with 100 ml of ether. The aqueous layer was then basified with K$_2$CO$_3$ and extracted with methylene chloride. The methylene chloride layer was acidified with ether-HCl and evaporated to dryness. The residue was crystallized in 2-propanol to give 12.5 g (54%) of product: m.p. 129° C.

EXAMPLES XV–LIII

The experiment of Example XIV was repeated in all essential details to produce the compounds identified in Table III, except the reactants listed in the second and third columns of the table were substituted for isopropylamine and 2-chlorobenzoyl chloride respectively. The compounds were prepared as the acid addition salts or free bases as indicated in Table III. Each of the compounds was identified by NMR and IR spectroscopy, elemental analysis, and melting point.

TABLE III $$Ar-\overset{O}{\underset{\|}{C}}-O-CH_2-\overset{OH}{\underset{|}{CH}}-CH_2-\underset{H}{\overset{|}{N}}-R$$

| Example | Reactants R−NH$_2$ | Reactants Ar−$\overset{O}{\underset{\|}{C}}$−Cl | Addition Salt | Ar | R | Crystallization Solvent | Melting Point |
|---|---|---|---|---|---|---|---|
| XV | isopropylamine | 1-naphthoyl chloride | HCl | 1-naphthyl | isopropyl | 2-propanol | 145–147° C. |
| XVI | isopropylamine | 2-naphthoyl chloride | HCl | 2-naphthyl | isopropyl | 2-propanol | 149.5–150° C. |
| XVII | isopropylamine | 2-methylbenzoyl chloride | HCl | 2-methylphenyl | isopropyl | 2-propanol | 120.5–121.5° C. |
| XVIII | isopropylamine | 2-fluorobenzoyl chloride | HCl | 2-fluorophenyl | isopropyl | acetone/ether | 144–145° C. |
| XIX | isopropylamine | 3-fluorobenzoyl chloride | HCl | 3-fluorophenyl | isopropyl | acetone/ether | 122.5–123° C. |
| XX | isopropylamine | 4-fluorobenzoyl chloride | HCl | 4-fluorophenyl | isopropyl | 2-propanol | 139–140° C. |
| XXI | isopropylamine | 3-nitrobenzoyl chloride | HCl | 3-nitrophenyl | isopropyl | 2-propanol | 160–160.5° C. |
| XXII | isopropylamine | 4-nitrobenzoyl chloride | HCl | 4-nitrophenyl | isopropyl | 2-propanol | 203–205° C. |
| XXIII | isopropylamine | 4-methoxybenzoyl chloride | HCl | 4-methoxyphenyl | isopropyl | 2-propanol | 139–140° C. |
| XXIV | isopropylamine | 4-cyanobenzoyl chloride | HCl | 4-cyanophenyl | isopropyl | 2-propanol | 167.5–168.5° C. |
| XXV | isopropylamine | 2-allyloxybenzoyl | oxalate | 2-allyloxyphenyl | isopropyl | 2-propanol | 133.5–135° C. |

TABLE III-continued $$Ar-\overset{\overset{O}{\|}}{C}-O-CH_2-\overset{\overset{OH}{|}}{CH}-CH_2-\underset{H}{N}-R$$

| Example | Reactants R—NH₂ | Ar—C(O)—Cl | Addition Salt | Ar | R | Crystallization Solvent | Melting Point |
|---|---|---|---|---|---|---|---|
| XXVI | isopropylamine | 3-allyloxybenzoyl chloride | HCl | 3-allyloxyphenyl | isopropyl | 2-propanol/ether | 111–112° C. |
| XXVII | isopropylamine | 2-n-propyloxybenzoyl chloride | oxalate | 2-n-propyloxyphenyl | isopropyl | 2-propanol | 131.5–132.5° C. |
| XXVIII | isopropylamine | 3-n-propyloxybenzoyl chloride | HCl | 3-n-propyloxyphenyl | isopropyl | 2-propanol/ether | 120–120.5° C. |
| XXIX | isopropylamine | 4-formylbenzoyl chloride | oxalate | 4-formylphenyl | isopropyl | 2-propanol | (hydroscopic) |
| XXX | isopropylamine | 4-benzyloxybenzoyl chloride | HCl | 4-benzyloxyphenyl | isopropyl | methanol | 137–137.5° C. |
| XXXI | 3,4-dimethoxy-phenethylamine | 2-methylbenzoyl chloride | oxalate | 2-methylphenyl | 3,4-dimethoxy-phenethyl | ethanol/2-propanol | 169–170° C. |
| XXXII | 3,4-dimethoxy-phenethylamine | 3-chlorobenzoyl chloride | oxalate | 3-chlorophenyl | 3,4-dimethoxy-phenethyl | 2-propanol | 183–186° C. |
| XXXIII | 3,4-dimethoxy-phenethylamine | 2-fluorobenzoyl chloride | HCl | 2-fluorophenyl | 3,4-dimethoxy-phenethyl | 2-propanol/ether | 109–110° C. |
| XXXIV | 3,4-dimethoxy-phenethylamine | 3-fluorobenzoyl chloride | oxalate | 3-fluorophenyl | 3,4-dimethoxy-phenethyl | 2-propanol | 171–171.5° C. |
| XXXV | 3,4-dimethoxy-phenethylamine | 4-fluorobenzoyl chloride | HCl | 4-fluorophenyl | 3,4-dimethoxy phenethyl | 2-propanol | 154–154.5° C. |
| XXXVI | 3,4-dimethoxy-phenethylamine | 4-nitrobenzoyl chloride | HCl | 4-nitrophenyl | 3,4-dimethoxy-phenethyl | 2-propanol | 162–163° C. |
| XXXVII | t-butylamine | benzoyl chloride | free base | phenyl | t-butyl | CCl₄/hexane | 105–106° C. |
| XXXVIII | t-butylamine | 2-chlorobenzoyl | free base | 2-chlorophenyl | t-butyl | CCl₄ | 74.5–75.5° C. |
| XXXIX | t-butylamine | 2-fluorobenzoyl chloride | free base | 2-flurophenyl | t-butyl | CCl₄ | 97.5–98° C. |
| XL | t-butylamine | 4-fluorobenzoyl chloride | free base | 4-fluorophenyl | t-butyl | CCl₄/hexane | 109–110° C. |
| XLI | t-butylamine | 2-methylbenzoyl chloride | free base | 2-methylphenyl | t-butyl | CCl₄/hexane | 93–94° C. |
| XLII | t-butylamine | 3-methylbenzoyl chloride | free base | 3-methylphenyl | t-butyl | CCl₄/hexane | 72–73° C. |
| XLIII | t-butylamine | 3-nitrobenzoyl chloride | free base | 3-nitrophenyl | t-butyl | CCl₄ | 91–92° C. |
| XLIV | t-butylamine | 4-nitrobenzoyl chloride | free base | 4-nitrophenyl | t-butyl | CCl₄/hexane | 106–107° C. |
| XLV | t-butylamine | 2-methyl-4-nitro-benzoyl chloride | HCl | 2-methyl-4-nitro-phenyl | t-butyl | 2-propanol | 170–171° C. |
| XLVI | t-butylamine | 2-benzyloxybenzoyl | free base | 2-benzyloxyphenyl | t-butyl | — | — |
| XLVII | t-butylamine | 3-benzyloxybenzoyl chloride | free base | 3-benzyloxphenyl | t-butyl | CCl₄/hexane | 100–101° C. |
| XLVIII | t-butylamine | 4-benzyloxybenzoyl chloride | oxalate | 4-benzyloxyphenyl | t-butyl | methanol | 173–174° C. |
| XLIX | t-butylamine | 4-allyloxybenzoyl chloride | oxalate | 4-allyloxphenyl | t-butyl | 2-propanol | 139–139.5° C. |
| L | t-butylamine | 4-n-butyloxy-benzoyl chloride | hemi-oxalate | 4-n-butyloxy-phenyl | t-butyl | 2-propanol | 196–197° C. |
| LI | t-butylamine | 1-naphthoyl chloride | oxalate | 1-naphthyl | t-butyl | 2-propanol | 165–166° C. |
| LII | t-butylamine | 4-formylbenzoyl chloride | oxalate | 4-formylphenyl | t-butyl | 2-propanol/ether | 170–171° C. |
| LIII | t-amylamine | 2-fluorobenzoyl chloride | free base | 2-fluorophenyl | t-amyl | CCl₄ | 50–51° C. |

EXAMPLE LIV

This example describes the synthesis of a compound of the formula

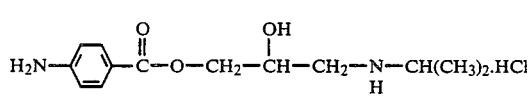

[2-Hydroxy-3-(isopropylamino)]propyl 4-aminobenzoate hydrochloride

To 20 mg of 10% Pd-C in 30 ml of methanol was added 0.4 g of the compound of Example XXII. The reaction vessel was kept under 30 p.s.i. of hydrogen and agitated for 1 hour. The catalyst was filtered and the methanol evaporated to give a solid, which was recrystallized in 2-propanol to give 220 mg (55%) of product: m.p. 211°–212° C. The NMR and IR spectra were consistent with the assigned structure and the elemental analysis was consistent with the empirical formula $C_{13}H_{21}N_2O_3Cl$.

EXAMPLES LV-LXI

The experiment of Example LIV was repeated in all essential details to produce the compounds identified in Table IV, except the starting materials described in the table were substituted for the compound of Example XXII. Each of the compounds was identified by NMR and IR spectroscopy, elemental analysis, and melting point.

TABLE IV

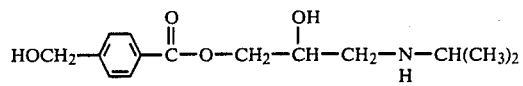

| Example | Starting Material (Example No.) | Ar | R | Addition Salt | Crystallization Solvent | Melting Point |
|---|---|---|---|---|---|---|
| LV | XXI | 3-aminophenyl | isopropyl | HCl | 2-propanol | 141–142° C. |
| LVI | XXX | 4-hydroxyphenyl | isopropyl | free base | 2-propanol/methanol | 170–170.5° C. |
| LVII | XLIII | 3-aminophenyl | t-butyl | oxalate | 2-propanol | 159.5° C. |
| LVIII | XLV | 2-methyl-4-aminophenyl | t-butyl | HCl | 2-propanol/ether | 209–210° C. |
| LIX | XLVI | 2-hydroxyphenyl | t-butyl | hemioxalate | methanol | 208–208.5° C. |
| LX | XLVII | 3-hydroxyphenyl | t-butyl | hemioxalate | methanol/acetone | 220–221° C. |
| LXI | XLVIII | 4-hydroxyphenyl | t-butyl | hemioxalate | 2-propanol/methanol | 220–220.5° C. |

EXAMPLE LXII

This example describes the synthesis of a compound of the formula

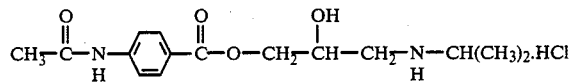

[2-Hydroxy-3-(isopropylamino)]propyl 4-(acetamido)benzoate hydrochloride

To 1 g (3.5 mmole) of the amine obtained in Example LIV in 30 ml of dried pyridine was added 0.32 g (4.55 mmol) of acetyl chloride. After stirring at room temperature for 2 hours the pyridine was evaporated in vacuo. The residue was partitioned between 5% $K_2CO_3$ and methylene chloride. The methylene chloride layer was acidified with ether-HCl and evaporated to dryness to give a gummy solid which was crystallized in acetone to give 0.38 g (33%) of product: m.p. 195° C. The NMR and IR spectra were consistent with the assigned structure and the elemental analysis was consistent with the empirical formula $C_{15}H_{23}N_2O_4Cl$.

EXAMPLE LXIII

The process in Example LXII was repeated in all essential details with the compound of Example LV as starting material and thus produced the compound: [2-Hydroxy-3-(isopropylamino)]propyl 3-(acetamido)-benzoate oxalate; m.p. 130°–132.5° C.

EXAMPLE LXIV

This example describes the synthesis of a compound of the formula $HOCH_2-$⟨⟩$-\overset{O}{\overset{\|}{C}}-O-CH_2-\overset{OH}{\overset{|}{CH}}-CH_2-\underset{H}{N}-CH(CH_3)_2$

[2-Hydroxy-3(isopropylamino)]propyl 4-(hydroxymethyl)benzoate hydrochloride

To a solution of 5.4 g (20.4 mmole) of the compound of Example XXIX in 20 ml of ethanol at 0° C. was added 0.8 g (20.4 mmole) of sodium borohydride. The reaction mixture was stirred at 0° C. for 10 minutes and excess hydride was destroyed by addition of water. The ethanol was evaporated to dryness and the residue was partitioned between 1% $K_2CO_3$ and methylene chloride. Evaporation of the methylene chloride gave an oil which was chromatographed on an alumina column using 10% ethanol in methylene chloride as the eluting solvent to give 32 mg (6) of the product: m.p. 98°–98.5° C. The NMR and IR spectra were consistent with the assigned structure and the elemental analysis was consistent with the empirical formula $C_{14}H_{21}NO_4$.

EXAMPLE LXV

This example describes the synthesis of a compound of the formula

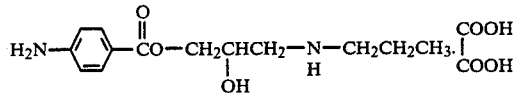

3-[N-(n-propyl)-N-benzyl]amino-1,2-propanediol

A mixture of 74 g (1 mole) of glycidol and 149 g (1 mole) of N-benzyl-N-isopropyl amine was stirred at 25° C. overnight. Distillation of the mixture gave 175.4 g (79%) of product: b.p. 135° C./0.5 mm Hg.

[3-[N-Benzyl-N-(n-propyl)]amino-2-hydroxy]propyl 4-nitrobenzoate

The diol from the previous experiment was allowed to react with p-nitrobenzoyl chloride in a similar manner as described in the preparation of [2-Hydroxy-3-(isopropylamino)]propyl 2-chlorobenzoate hydrochloride in Example XIV. The product was purified by chromatography (silica gel/ether:hexane=4:2). Yield was 65%.

[2-Hydroxy-3-(n-propyl)amino]propyl 4-aminobenzoate oxalate

The amine 12 g (33 mmole) from the previous experiment was mixed with 50 ml of 2-propanol-ethanol (1:1), 2.97 g (33 mmole) of oxalic acid and 0.24 g of 10% Pd-C. The reaction vessel was pressurized with 50 p.s.i. of H₂ and agitated for 16 hours at room temperature. The reaction mixture was filtered. Evaporation of the 2-propanol from the filtrate resulted in crystallization of the product; 2.4 g (22%): m.p. 173° C. The NMR and IR spectra were consistent with the assigned structure and the elemental analysis was consistent with the empirical formula $C_{15}H_{22}N_2O_7$.

EXAMPLE LXVI

This example describes the synthesis of a compound of the formula

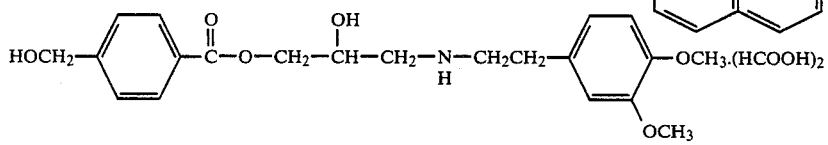

3-[N-[(4-methoxybenzyl)oxycarbonyl]-N-(3,4-dimethoxyphenethyl)]amino-1,2-propanediol]

A mixture of 26 g (0.102 mole) of 3-(3,4-dimethoxyphenethyl)amino-1,2-propanediol, 29 g (0.345 mole) of sodium bicarbonate and 24 g (0.116 mole) of p-methoxybenzyloxycarbonyl azide in 200 ml of dioxane and 10 ml of water was stirred at room temperature for 24 hours. After evaporation of the dioxane in vacuo, the residue was partitioned between water and CHCl₃. Evaporation of CHCl₃ gave an oil which was purified by chromatography (silica gel/10% ethanol in methylene chloride) to give 13 g (30.5% of product.

2-Hydroxy-3-[[N-[(4-Methoxybenzyl)oxycarbonyl]-N-(3,4-dimethoxyphenethyl)]propyl 4-formylbenzoate The diol from the previous experiment was allowed to react with 4-formylbenzoyl chloride in a similar manner as described in the preparation of [2-Hydroxy-3-(isopropylamino)]propyl 2-chlorobenzoate hydrochloride in Example XIV. The product was purified by chromatography (silica gel/2% ethanol in ether). The yield was 27%.

2-Hydroxy-3-[N-(3,4-dimethoxyphenethyl)amino]propyl 4-(hydroxymethyl) benzoate oxalate The aldehyde obtained from the previous experiment was reduced by sodium borohydride in a similar manner as described in Example LXIV. The crude product was dissolved in ether-HCl was stirred at room temperature for 2 hours. The ether was evaporated to dryness and the product was partitioned between 5% K₂CO₃ and methylene chloride. A solution of oxalic acid in 2-propanol was added to the methylene chloride layer and the precipitate was recrystallized in ethanol to give the desired product in 19% yield; m.p. 164°–164.5° C. The NMR and IR spectra were consistent with the assigned structure and the elemental analysis was consistent with the empirical formula $C_{23}H_{29}NO_{10}$.

EXAMPLE LXVII

The experiment of Example I is employed to produce a compound of the formula

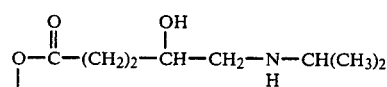
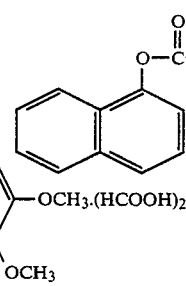

The procedure is repeated in all essential details, except 4-hydroxy-5-chloropentanoic acid is substituted for β-chlorolactic acid and isopropylamine is substituted for 3,4-dimethoxyphenethylamine to produce the intermediate 5-isopropylamino-4-hydroxypentanoic acid. The hydroxy and amino groups are protected as described in Example I. The resulting acid is reacted with 1-naphthol instead of phenol and the protecting groups are removed as in Example I. The resulting compound should be a short acting β-blocker.

EXAMPLE LXVIII

The experiment of Example V is employed to produce a compound of the formula

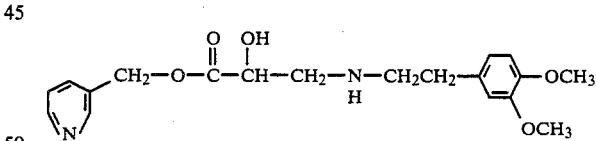

The procedure is repeated in all essential details, except 3-hydroxymethylpyridine is substituted on a molar basis for 2-methoxybenzyl alcohol. The product should be a short acting β-blocker.

TABLE V

| Example | Test Compound (Numerical designation indicates previous example which describes preparation of compound) | pA₂ Atria | pA₂ Trachea | Cardioselectivity $K_B$(Trachea)/$K_B$(Atria) |
|---|---|---|---|---|
| LXIX | VI | 6.3 | 7.2 | −7 |
| LXX | XVIII | 6.6 | 7.1 | −3 |
| LXXI | XII | 6.8 | 7.4 | −4 |
| LXXII | XXVII | 6.6 | — | — |
| LXXIII | XIX | 6.5 | 7.0 | −3 |
| LXXIV | XXI | 6.8 | 7.2 | −2.5 |
| LXXV | LV | 6.4 | 6.8 | −2.5 |
| LXXVI | VIII | 6.8 | 7.3 | −3 |
| LXXVII | XX | 6.6 | 7.3 | −5 |

TABLE V-continued

| Example | Test Compound (Numerical designation indicates previous example which describes preparation of compound) | pA₂ Atria | pA₂ Trachea | Cardioselectivity K_B(Trachea)/K_B(Atria) |
|---|---|---|---|---|
| LXXVIII | XXII | 6.1 | 6.2 | 1 |
| LXXIX | X | 6.8 | 6.8 | 1 |
| LXXX | XXIII | 6.0 | 6.3 | −2 |
| LXXXI | XXIV | 5.7 | 5.7 | 1 |
| LXXXII | LVI | 6.8 | 7.2 | −2.5 |
| LXXXIII | LXIV | 6.2 | 6.3 | 1 |
| LXXXIV | LXII | 5.8 | 5.2 | 4 |
| LXXXV | XXX | <6.0 | — | — |
| LXXXVI | XXXVII | 6.8 | 7.7 | −8 |
| LXXXVII | XXXIX | 6.8 | 8.0 | −16 |
| LXXXVIII | XXXVIII | 7.2 | 7.8 | −4 |
| LXXXIX | LIII | 6.8 | — | — |
| XC | VII | 7.0 | 6.3 | 5 |
| XCI | XXXIII | 6.1 | 5.7 | 2.5 |
| XCII | XIII | 7.8 | 7.5 | 2 |
| XCIII | XXXIV | 6.4 | 6.2 | 2 |
| XCIV | IX | 6.9 | 6.6 | 2 |
| XCV | XXXV | 7.0 | 6.7 | 2 |
| XCVI | XI | 6.6 | 6.0 | 4 |
| XCVII | LXVI | <5.5 | — | — |
| XCVIII | I | 5.9 | 5.9 | 1 |
| XCIX | II | 5.9 | — | — |
| C | V | inactive | 5.0 | — |
| CI | XV | 6.6 | 7.0 | −2.5 |
| CII | XVI | 6.4 | 6.6 | −2 |
| CIII | LXV | 5.9 | — | — |

EXAMPLES LXIX–CIII

Several of the compounds of the present invention were tested for β-blocking activity in vitro using guinea pig right atria and guinea pig tracheal strips mounted in a tissue bath containing oxygenated (95% $O_2$-5% $CO_2$) Krebs physiological salt solution at 37° C. Each tissue was suspended between a fixed glass rod and a Statham ® Universal Transducer connected to a Beckman ® recorder. Atria were allowed to beat spontaneously under a loading tension of approximately 0.5 gm. Instrinsic depressant or stimulant activity was determined for each compound by progresssively increasing concentrations in the tissue baths at 60-minute intervals. Tissues were not washed between increments. The maximum concentration showing little or no cardiodepressant activity was chosen for blockade experiments. Changes in rate in response to isoproterenol were measured in the absence and presence of test compounds. Spiral strips of guinea pig trachea were suspended under 5 gm resting tension and incubated with phentolamine, tropolone and cocaine. Active tension was generated by addition of carbachol ($3.0\times10^{-7}$M) and decreases in tension in response to isoproterenol were quantitated. Cumulative concentration-response curves were produced with isoproterenol both before and after 60 minute incubation of test compounds with atria and trachea. The blocking potency of test compounds was estimated by computing pA₂ values ($-\log K_8$) by the method of Furchgott, The Pharmacological Differentiation of Adrenergic Receptors, Ann. N.Y. Acad. Sci., 139: 553–570 (1967). Comparison of blockade of right atrial and tracheal responses to isoproterenol permitted assessment of cardioselectivity of test compounds, i.e., cardioselective compounds are relatively more effective in blocking atrial rate than tracheal force response to isoproterenol. The degree of cardioselectivity was estimated from the ratio, $K_B$ trachea/$K_B$ atria ($10^{(pA2atria-pA2trachea)}$). A ratio greater than one indicates cardioselectivity. Test drugs were dissolved in distilled water and added to the bath (30 ml) in a volume of 10 or 100 μl. The results of the in vitro tests are contained in Table V. All of the test compounds were active β-blockers.

EXAMPLES CIV–CXXVIII

The duration of beta-blockade was determined in vivo using pentobarbital-anesthetized dogs instrumented for measurement of heart rate using a Beckman ® cardiotachometer triggered electronically by a phasic aortic blood pressure signal. Both vagus nerves were severed in the cervical region and the animals were mechanically ventilated. Two experimental designs were used. The first employed a 40-minute infusion of test compound and the second used a 3-hour infusion of test compound. In the 40-minute model, isoproterenol was infused into a foreleg vein at the rate of 0.5 μg/kg/min to induce a beta-receptor mediated tachycardia. Various doses of test compound where then infused into a femoral vein over a period of 40 minutes. This infusion was then terminated and recovery from blockade was quantitated. The percent inhibition of the heart rate response to isoproterenol after 40 minutes of infusion of the test compound was computed along with the total cumulative doses received over the 40-minute period. This cumulative dose is expressed as mg/kg and is an indication of potency. The time period required for 80% recovery of heart rate for each dose of test drug was also measured to quantitate duration of action. To facilitate comparison of data between animals, the data for potency and duration of action were normalized to a level of 50% inhibition of the isoproterenol response via least squares regression of data from each animal. Test compounds were dissolved in 0.9% NaCl and infused at a rate of 0.05 ml/kg/min or less. In the 3-hour infusion model, bolus doses of isoproterenol (0.5 μg/kg) were used to assess the degree of beta-blockade and recovery from beta-blockade after termination of the infusion. The doses were spaced at 10-minute intervals and were given before, during and following the infusion of test compounds. The infusion rate was adjusted so that at the end of the 3-hour infusion period the degree of isoproterenol inhibition averaged about 50% of control. The results of the 40-minute infusion are shown in Table VI, and the results of the 3-hour infusion are shown in Table VII.

tor for 2.5, 5.0, 10.0, 20.0, 30.0 and 60.0 minutes at 37° C. At the designated time periods, the test mixtures were removed from the incubator and transferred to a 0° C. ice bath. Acetonitrile (2 ml) was immediately added and

TABLE VI

| Example | Test Compound (Numerical designation indicates previous example which describes preparation of compound) | Potency (mg/kg) | Recovery Times (min.) 50% | 80% | 100% |
|---|---|---|---|---|---|
| CIV | XV | 1.5 | 18 | 22 | 38 |
| CV | VI | 3.4 ± 1.1 | 7 ± 2 | 14 ± 3 | 21 ± 3 |
| CVI | I | 3.5 ± 0.5 | 6 ± 1 | 11 ± 1 | 16 ± 2 |
| CVII | V | low | — | — | — |
| CVIII | VIII | 1.83 ± .11 | 7 ± 1 | 14 ± 3 | 20 ± 4 |
| CIX | X | 3.1 ± 0.3 | 11.0 | 20 ± 2 | 30.0 |
| CX | XIII | 2.0 ± 0.6 | 7 | 12 ± 1 | 24 |
| CXI | IX | 4.7 ± 1.7 | 6 ± 1 | 10 ± 1 | 16 ± 2 |
| CXII | XI | 17.2 ± 5.8 | 8 ± 1 | 16 ± 2 | 25 ± 3 |
| CXIII | XII | 1.75 | 19 | 30 | 51 |
| CXIV | XVIII | 1.5 | — | 8 ± 1 | — |
| Propranolol | — | — | 23 ± 4 | 42 ± 8 | 58 ± 9 |

TABLE VII

| Example | Test Compound | Potency (mg/kg/180 min) | % I* | 80% Recovery Time (min) | No. of Experiments |
|---|---|---|---|---|---|
| CXV | VI | 23.04 | 63 ± 8 | 26 ± 8 | (4) |
| CXVI | VII | 21.76 | 45 ± 2 | 29 ± 5 | (8) |
| CXVII | XXXIX | 3.6 ± 0.6 | 60 ± 2 | 17 ± 3 | (5) |
| CXVIII | XVIII | 19.08 | 46 ± 5 | 25 ± 9 | (7) |
| CXIX | LIV | 1.25 | 80 ± 4 | >60 | (3) |
| CXX | XXXV | 10.7 | 59 | >60 | (2) |
| CXXI | XV | 32.7 | 54 | >60 | (2) |
| CXXII | XVII | 9.0 | 83 | >60 | (2) |
| CXXIII | XXXI | 40.7 | 85 | >60 | (2) |
| CXXIV | XXIII | 37.6 | 67 ± 6 | >60 | (3) |
| CXXV | XXXVIII | 3.2 | 67 | 35, >60 | (2) |
| CXXVI | LVI | 4.5 | 79 ± 9 | 45, >60, >60 | (3) |
| CXXVII | XXXVII | 12.6 | 64 ± 5 | >60 | (4) |
| CXXVIII | XXVII | 31.0 | 69 | >60 | (2) |
| Propranolol | | 0.225 | | >60 | (6) |

*Percent inhibition of heart rate response to isoproterenol.

EXAMPLES CXXIX–CXLII

These examples describe experiments which demonstrate the disappearance of the compounds of the present invention in vitro in human whole blood, dog whole blood, and dog liver homogenate. The rate of disappearance of a compound is expressed as the half-life ($T_{\frac{1}{2}}$), which is the time period in which one half of the initial amount of compound tested disappears. In each experiment, 1 ml. of a solution containing 50 μg of the test compound was added to 1 ml. of whole blood or 1 ml. of a 33% (w/v) liver homogenate. The samples were incubated in a Dubnoff shaking metabolic incubator for 2.5, 5.0, 10.0, 20.0, 30.0 and 60.0 minutes at 37° C. At the designated time periods, the test mixtures were removed from the incubator and transferred to a 0° C. ice bath. Acetonitrile (2 ml) was immediately added and the mixtures were mixed to stop enzymatic hydrolysis. Zero time samples were prepared by adding 2 ml. of acetonitrile to denature the proteins prior to addition of the test compounds. After centrifugation to sediment denatured proteins, 2 ml. of the supernatant was removed and analyzed by high pressure liquid chromatography, using a mobile phase of 60% acetonitrile/40% 0.05 m sodium phosphate buffer (pH 6.6), a U.V. detector and Waters ® μ Bondapak Phenyl column. The half life of each test compound was determined graphically by plotting the decrease in concentration as a function of time. The results of the experiments are shown in Table VIII.

TABLE VIII

| Example | Test Compound (numerical designation indicates previous example which describes preparation of compound) | $T_{\frac{1}{2}}$ (minutes) Human Whole Blood | Dog Whole Blood | Dog Liver Homogenate |
|---|---|---|---|---|
| CXXIX | XVIII | 1.7 ± 0.6 | 7 | — |
| CXXX | XII | 1.7 ± 0.6 | 28 ± 15 | 12 ± 4 |
| CXXXI | VI | 2.3 ± 0.6 | 6.8 ± 2 | 8.0 ± 3.5 |
| CXXXII | XX | 3.5 ± 0.9 | 4 | — |
| CXXXIII | X | 6 ± 0 | 67 ± 24 | 10 ± 4 |
| CXXXIV | XIX | 8 ± 4 | 50 | — |
| CXXXV | XXIII | 55 ± 5 | 150 ± 30 | 37 ± 20 |
| CXXXVI | XVII | >>180 | >>180 | 147 ± 69 |
| CXXXVII | XXXIX | 1.4 ± 1 | 6 ± 2 | 17 ± 7 |
| CXXXVIII | XXXVII | 5.3 ± 1 | 5.5 | — |
| CXXXIX | XLII | 5.5 ± 2.6 | 150 | — |
| CXL | XXXVIII | 6 ± 2 | 30 ± 2 | 68 ± 4 |
| CXLI | XL | 11 ± 5 | 13 | — |

We claim:
1. A compound of the formula

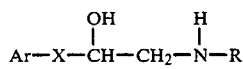

wherein Ar is unsubstituted phenyl, phenyl substituted with fluoro in the ortho position, or phenyl substituted with methyl in the meta or para position; X is

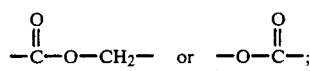

and R is isopropyl, t-butyl or 3,4-dimethoxyphenethyl; with the proviso that when Ar is unsubstituted phenyl, or 4-methylphenyl R is isopropyl or 3,4-dimethoxyphenethyl; and with the further proviso that when X is

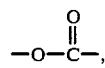

Ar is unsubstituted phenyl and R is 3,4-dimethoxyphenethyl; or a pharmaceutically acceptable salt thereof.

2. The compound of claim 1 wherein Ar is phenyl substituted with fluoro in the ortho position; X is

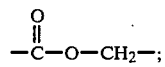

and R is isopropyl, t-butyl or 3,4-dimethoxyphenethyl; or a pharmaceutically acceptable salt thereof.

3. The compound of claim 1 wherein Ar is phenyl substituted with methyl in the meta or para position; X is

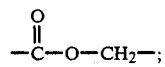

and R is isopropyl, t-butyl or 3,4-dimethoxyphenethyl; or a pharmaceutically acceptable salt thereof.

4. The compound of claim 1 wherein Ar is unsubstituted phenyl; X is

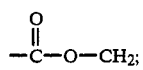

or R is isopropyl or 3,4-dimethoxyphenethyl; or a pharmaceutically acceptable salt thereof.

5. The compound of claim 1 wherein Ar is unsubstituted phenyl, X is

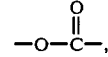

and R is 3,4-dimethoxyphenethyl.

6. The compound of claim 1 wherein Ar is phenyl substituted with fluoro in the ortho position, X is

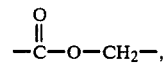

and R is isopropyl, or a pharmaceutical acceptable salt thereof.

7. The compound of claim 1 wherein Ar is phenyl substituted with fluoro in the ortho position, X is

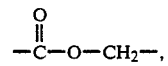

and R is t-butyl, or a pharmaceutically acceptable salt thereof.

8. The compound of claim 1 wherein Ar is phenyl substituted with fluoro in the ortho position, X is

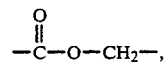

and R is 3,4-dimethoxyphenethyl, or a pharmaceutically acceptable salt thereof.

9. The compound of claim 1 wherein Ar is phenyl substituted with methyl in the meta position, X is

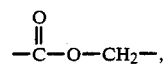

and R is isopropyl, or a pharmaceutically acceptable salt thereof.

10. The compound of claim 1 wherein Ar is phenyl substituted with methyl in the meta position, X is

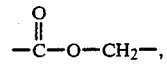

and R is t-butyl, or a pharmaceutically acceptable salt thereof.

11. The compound of claim 1 wherein Ar is phenyl substituted with methyl in the meta position, X is

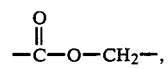

and R is 3,4-dimethoxyphenethyl, or a pharmaceutically acceptable salt thereof.

12. The compound of claim 1 wherein Ar is phenyl substituted with methyl in the para position,

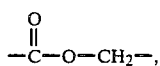

and R is isopropyl, or a pharmaceutically acceptable salt thereof.

13. The compound of claim 1 wherein Ar is phenyl substituted with methyl in the para position, X is

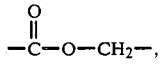

and R is t-butyl, or a pharmaceutically acceptable salt thereof.

14. The compound of claim 1 wherein Ar is phenyl substituted with methyl in the para position, X is

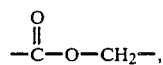

and R is 3,4-dimethoxyphenethyl, or a pharmaceutically acceptable salt thereof.

15. The compound of claim 1 wherein Ar is unsubstituted phenyl, X is

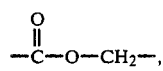

and R is isopropyl, or a pharmaceutically acceptable salt thereof.

16. The compound of claim 1 wherein Ar is unsubstituted phenyl, X is

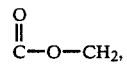

and R is 3,4-dimethoxyphenethyl, or a pharmaceutically acceptable salt thereof.

* * * * *